United States Patent
Sarkisov et al.

(10) Patent No.: US 7,842,243 B2
(45) Date of Patent: Nov. 30, 2010

(54) CHEMICAL SENSOR WITH AN INDICATOR DYE

(76) Inventors: Sergey Sergeyevich Sarkisov, 2305 Fleet Cir., Huntsville, AL (US) 35803; Wiaczeslaw Mazuruk, 13025 Macbeth Dr., Huntsville, AL (US) 35803

( * ) Notice: Subject to any disclaimer, the term of this patent is extended or adjusted under 35 U.S.C. 154(b) by 957 days.

(21) Appl. No.: 11/707,810

(22) Filed: Feb. 17, 2007

(65) Prior Publication Data

US 2008/0233008 A1    Sep. 25, 2008

Related U.S. Application Data

(60) Provisional application No. 60/774,488, filed on Feb. 21, 2006, provisional application No. 60/817,197, filed on Jun. 29, 2006.

(51) Int. Cl.
    *G01N 21/00* (2006.01)
(52) U.S. Cl. .................. 422/82.11; 422/56; 422/57; 422/82.05; 422/83; 436/169; 356/73.1; 356/128; 385/143; 385/145
(58) Field of Classification Search ............ 422/82.05, 422/83, 56, 57, 82.11; 356/73.1, 128; 385/143, 385/145; 436/169
See application file for complete search history.

(56) References Cited

U.S. PATENT DOCUMENTS

| 4,513,087 | A |   | 4/1985 | Giuliani et al. |              |
|-----------|---|---|--------|-----------------|--------------|
| 4,761,710 | A |   | 8/1988 | Chen            |              |
| 5,640,234 | A | * | 6/1997 | Roth et al.     | ...... 356/128 |
| 5,774,603 | A | * | 6/1998 | Moore et al.    | ...... 385/12  |
| 6,778,316 | B2| * | 8/2004 | Halas et al.    | ...... 359/296 |

OTHER PUBLICATIONS

Sarkisov et al, "Planar optical waveguide sensor of ammonia", Dec. 7, 2004, Advanced Environmental, Chemical, and Biological Sensing Technologies II, vol. 5586, pp. 33-44.*

Dakin, J., and Culshaw, B., Optical fiber sensors. vol. 4: Applications, Analysis, and Future Trends, Artech House, Boston, 1997, pp. 53-80 and pp. 95-97.

Boisde, G., and Harmer, A., Chemical and biochemical sensing with optical fibers and waveguides, Artech House, Boston, 1996, pp. 65-84.

(Continued)

*Primary Examiner*—Lyle A Alexander
*Assistant Examiner*—Dennis M White
(74) *Attorney, Agent, or Firm*—James Richards

(57) ABSTRACT

A chemical sensor based on an indicator dye wherein a light transmissive element containing the indicator dye is made of a hygroscopic polymer. The polymer may be, for example, a polyimide or PMMA or other polymer. In an alternative embodiment the light transmissive element is doped with metal nanocolloidal particles. One embodiment may include a reference photodiode and differential amplifier to compensate for the fluctuations of the intensity of the light source. The light source may be pulse modulated. The sensor may include calibration means comprising a reference sample of the chemical to be detected and a precision delivery means. A method of fabricating the polymer and metal nanocolloid is disclosed wherein the nanocolloid is produced by generating a pulsed laser plasma in a suspension of metal particles and an organic solvent and adding the resulting solvent colloid to a solution containing the polymer.

18 Claims, 12 Drawing Sheets

OTHER PUBLICATIONS

Klein, R., and Voges, E.I., "Integrated optics ammonia sensor," Advances in fluorescence sensing technology, edited by J.R. Lakowicz and R.B. Thompson, Proceedings of SPIE, vol. 1885, SPIE, Bellingham, WA, 1993, 81-92.

Caglar, P., and Narayanaswamy, R., "Ammonia-sensitive fibre optic probe utilizing an immobilized spectrophotometric indicator," Analyst, vol. 112, 1987, pp. 1285-1288.

Hartman; N.F., Walsh, J.L., Campbell, D.P., and Akki, U., "Integrated optic gaseous NH3 sensor for agricultural applications," Optics in Agriculture, Forestry, and Biological Processing, edited by G.E. Meyer and J. A. DeShazer, Proceedings of SPIE, vol. 2345, SPIE, Bellingham, WA, 1995, pp. 314-323.

Bowman, E.M. and Burgess L.W., "Evaluation of polymeric thin film waveguides as chemical sensors," Chemical, Biochemical, and Environmental Fiber Sensors II, Proceedings of SPIE, vol. 1368, SPIE, Bellingham, WA, 1990, 239-250.

Lieberman, R.A., Ferrell, D.J., Schmidlin, E.M., Syracuse, S.J., Khalil, A.N., Mendoza, E.A., "Reversible sensor for carbon monoxide based on dye-doped porous fiber optic fiber," Proceedings of SPIE, vol. 1796, SPIE, Bellingham, WA, 1992, 324-331.

Zh. Qi, A. Yimit, K. Itoh, M. Murabayashi, N. Matsuda, A. Takatsu, and K. Kato, Composite optical waveguide composed of a tapered film of bromothymol blue evaporated onto a potassium ion-exchanged waveguide and its application as a guided wave absorption-based ammonia gas sensor, Opt. Lett., vol. 26, No. 9, 2001, 629-631.

Hummel, Rolf E. and Wismann, P., "Handbook of Optical Properties, vol. II, Optics of Small Particles, Interfaces, and Surfaces" CRC Press, Inc. 1997 pp. 191-197.

Pranjoto, Hartono and Denton, Denice "Gravimetric measurements of steady state moisture uptake in spin coated polyimide films" Journal of Applied Polymer Science vol. 42, Issue 1, abstract for pp. 75-83, Mar. 10, 2003.

Amoco Chemical, "Ultradel 9020D Coatings" Bulletin UL-P13.

Amoco Chemical, "Ultradel 9020D Process Guidelines" Bulletin UL-PG7.

Cahill, PA, et al. "Polyimide Based Electrooptic Materials" Nonlinear Optical Properties of Organic Materials VI, Jul. 13, 1993, Society of Photo-Optical Instrumentation Engineers, pp. 48-55.

Sarkisov, Sergey et al. "Single-arm double-mode double-order planar waveguide interferometric sensor," Applied Optics, Jan. 20, 2001, vol. 40, No. 3, Optical Society of America, pp. 349-359.

Yimit, Abliz et al. "Detection of Ammonia in the ppt range based on a composite optical waveguide pH sensor," Sensors and Actuators B 88 (2003) pp. 239-345, 2002 Elsevier Science B. V.

Giuliani, J.F. et al., "Reversible optical waveguide sensor for ammonia vapors," Optics Letters, vol. 8, No. 1, Jan. 1983, Optical Society of America, pp. 54-56.

Siegel, R. W., Hu, E., and Roco, M.C., editors "Nanostructure Science and Technology: R&D Status and Trends in Nanoparticles, Nanostructured Materials, and Nanodevices." National Science and Technology Council. Kluwer Academic Publishers, 1999, Chapters 2, 7. PDF document.

* cited by examiner

CHEMICAL SENSOR WITH AN INDICATOR DYE

RELATED APPLICATIONS

The present application claims the benefit under 35 USC 119(e) of prior U.S. Provisional Application 60/774,488 titled "Chemical Sensor," filed Feb. 21, 2006 by Sarkisov et al, and U.S. Provisional Application 60/817,197, titled "Method And Apparatus For Laser Spark Crushing Of Micropowder Into Nanopowder," filed Jun. 29, 2006 by Sarkisov et al, both of which are incorporated herein by reference in their entirety.

BACKGROUND

1. Field of the Invention

The present invention pertains generally to the field of chemical sensors, more particularly, to the field of chemical sensors based on indicator dyes.

2. Background of the Invention

Optical sensors of gaseous pollutants in air based on indicator dyes have recently become fast expanding technology (see References 1 and 2). There are some features of these sensors that attract potential users: simplicity, compactness, ruggedness, robustness, and tolerance of electro-magnetic interference. The major problem of these sensors has been their poor sensitivity. Attempts to address this problem are often based on increasing the length of interaction of light with medium containing indicator dye. Longer interaction length is usually achieved by letting the light to pass through a light guiding structure either filled with the indicator dye or having an optical contact with the medium containing the dye.

In Reference 3, Klein et al. teach that a chemical sensor can be made as a strip multi-mode waveguide fabricated by a field-assisted ion-exchange in B-270 glass spin-coated with a porous sol-gel layer that has an immobilized indicator dye (bromocresol purple) sensitive to ammonia Light from two light-emitting diodes, at 600 and 700 nm, was sent through a standard gradient-index optical fiber. The fiber was butt-coupled with the waveguide at one of its ends. The other flat end was coated with a reflective aluminum coating. After passing through the waveguide, the light was reflected by the aluminum mirror back into the fiber. The intensity of light at each wavelength (600 and 700 nm) was modulated at its own distinguished frequency. After receiving light back from the fiber, a lock-in amplifier was used to extract signals proportional to the intensity at 600 and 700 nm respectively. At the presence of ammonia, only light at 600 nm experienced drop in intensity due to the reversible increase of absorption of the indicator dye exposed to ammonia. Division of the signal proportional to 600-nm intensity by the 700-nm signal with an electronic divider eventually produced an output signal that is proportional to the concentration of ammonia. The process of fabrication of the waveguide is complex and costly. Coupling of the multi-mode fiber with the waveguide requires special alignment and some means, not specified, of fixing the fiber to the waveguide.

In Reference 4, Caglar et al. teach that the chemical sensor can be made by attaching to the end of a plastic optic fiber a cluster of AMBERLITE XAD-7™ polymer micro-beads with an immobilized indicator dye, bromothymol blue. The light sent through the fiber is reflected back from the cluster. The intensity of the reflected light decreases when the cluster is exposed to ammonia thus producing a sensing effect. However, the size of the region where the reflected light interacts with the exposed beads is very short, a few microns. The sensitivity of the sensor is relatively poor.

In References 5 and 6, Hartman et al. and Bowman et al. teach that the chemical sensor can monitor changes in the refractive index of a polymer where the sensor can be made as a planar slab waveguide with gratings as means of coupling light with the waveguide. The polymer is poly(vinyl alcohol), polyimide CIBA-Geigy Probimide 285, dimethylsiloxate bis-phenol copolymer PS254 from Petrarch Systems Inc., and hard silicone OF20 from Shin-Etsu Chemical Co. Fabrication of gratings requires rather costly photolithographic process to be used. Change of the refractive index of the light guiding layer due to exposure to an analyte or due to variation of temperature changes the efficiency of coupling thus affecting the reading of the sensor.

In Reference 7, Lieberman et al. teach that a sensor of carbon monoxide can be made using a tip of a specially processed dye-doped porous optic fiber (multimode porous silica fiber, 2-8-nm pore diameter, 2 cm in length, and 250 micron in diameter) as a sensing element. This sensor requires a special, rather complex, procedure of preparation of the porous fiber and filling it with sensitive dye. The length of interaction of light with the sensitive material cannot be made large due to effects of scattering. The sensitivity of the sensor remains poor.

In Reference 8, Qi et al. teach that the sensor of ammonia can be made using a layer of indicator dye bromothymol blue deposited by vacuum evaporation on an ion-exchanged glass waveguide. However, conventional prism couplers are mechanically attached to the waveguide from the side of the ambient air. This makes the couplers and other optical elements open to the possible harmful effects of ammonia as well as to dust and atmospheric moisture.

In U.S. Pat. No. 4,513,087, Giuliani et al. describe a sensor wherein the principle of operation is based on transmitting light through an optical waveguide coated with an oxazine perchlorate dye film whose optical absorption between 500 and 700 nm changes from high to low when exposed to ammonia, hydrazine, or pyridine and returns to its original high level when the chemical is removed. The sensor consists of an optical waveguide made from a glass capillary tube with two flat ends. The outer wall of the tube is spray-coated (from a solution) with an oxazine perchlorate dye film. The tube is surrounded by a cell with inlet and outlet for letting the gas in and out. A light source, including a light-emitting diode (LED) and a flasher connected to LED, is optically "butt" coupled to one end of the tube. A light sensor, including a phototransistor, is optically butt coupled to another end of the tube to receive the light pulses and convert them to electrical pulses. Butt coupling to the tube is simply achieved by putting LED and phototransistor in mechanical contact with the tube. Coupling is simple and requires no alignment. Coupling efficiency is less sensitive to moderate mechanical vibrations. An amplifier is connected to the light sensor for amplifying the electrical pulses. A rectifier is connected to the amplifier to rectify the amplified pulses. A filter is connected to the rectifier to smoothen an output signal from rectifier. An indication device (chart recorder) is connected to the filter for showing the concentration of the gas passing through the cell.

The disadvantages of the Giuliani sensor are:

1) Sensitivity is poor.

2) The sensitive coating is sensitive to atmospheric moisture: the reading of the sensor fluctuates when the relative humidity changes.

3) The sensor is open to the noise produced by the slow fluctuations of the intensity of the light source and the noise produced by rapid fluctuations of ambient light and by the photodetector.

4) The sensor lacks means of self-calibration for achieving high accuracy.

All the proposed solutions to the problem of poor sensitivity rely on some sort of light guiding structure, planar waveguide or optical fiber, which requires rather complex techniques of coupling light with the structure that makes sensor expensive and vulnerable to mechanical vibrations. Besides that, dependence of the response of the sensor to atmospheric moisture, fluctuations of the intensity of the light source in combination with the noise produced by ambient light and photodetector, and the lack on any means of self-calibration have to be addressed.

To summarize, there is a great need for an inexpensive chemical sensor with the following characteristics:

1) a higher sensitivity should be achieved with a simple and reliable technique resistant to contamination and tolerant of a wide temperature range;

2) the effect of atmospheric moisture should be reduced;

3) the effects of noise originating from the fluctuations of the intensity of the light source as well as the noise produced by ambient light and the photodetector should be reduced; and 4) a self-calibration feature should be provided.

BRIEF DESCRIPTION OF THE INVENTION

Briefly, the present invention is related to a chemical sensor based on an indicator dye wherein a light transmissive element containing the indicator dye is made of a hygroscopic polymer. The polymer may be, for example, a polyimide or poly(methyl methacrylate) known as PMMA. In an alternative embodiment, the light transmissive element is doped with metal nanoparticles.

One embodiment may include a reference photodiode and differential amplifier to compensate for the fluctuations of the intensity of the light source.

In another embodiment, the light source may be pulse modulated and sensed by a lock-in amplifier and detector synchronized to the pulse signal that drives the light source.

In a further embodiment, the sensor may include calibration means comprising a reference container containing a reference sample of the chemical to be detected and a delivery means to deliver a precise concentration of the reference sample to the detector.

In a further embodiment, the sensor may sense a gas in air, or alternatively a chemical in a fluid, such as water.

The sensor may be used in an air environment having a variable relative humidity.

A method of fabricating the polymer and metal nanocolloid is disclosed wherein the nanocolloid is produced by generating a pulsed laser plasma in a suspension of metal particles and an organic solvent and adding the resulting solvent colloid to a solution containing the polymer.

These and further benefits and features of the present invention are herein described in detail with reference to exemplary embodiments in accordance with the invention.

BRIEF DESCRIPTION OF THE FIGURES

The present invention is described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION OF THE INVENTION

Figure 1:
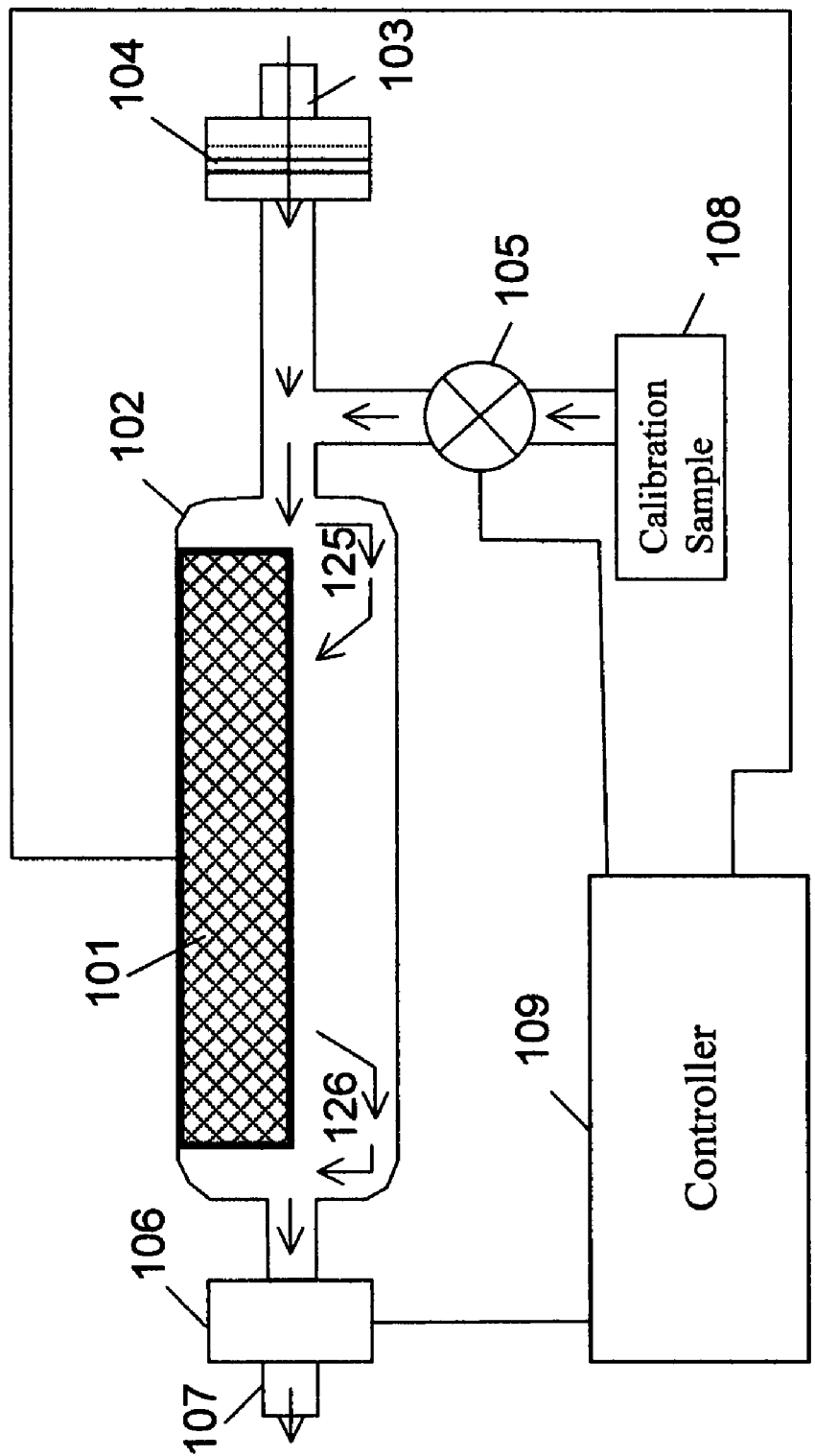
FIG. 1 is a block diagram of an exemplary sensor in accordance with the present invention.

One objective of the present invention is to produce a chemical sensor that may be used in the field for sensing gasses such as pollutants, in particular ammonia and related species. The sensor should operate in harsh field environments over a wide variety of applications. Applications may range from factory smoke stacks, processing bins, poultry houses, chemical storage areas to rocket launch pads. Field conditions vary considerably in temperature and humidity and may be subject to dust and condensing fogs or mists. Further, the sensor should operate for extended periods of time without having to be serviced or replaced.

The present invention pertains to a chemical sensor and a method of sensing a chemical analyte in a fluid or gas. The sensor is based on sensing a change in the optical transmission through a medium containing an indicator dye.

Generally, the invention relates to the detection of basic gas analytes, including, but not limited to, hydrazine, alkyl hydrazines, amines, ammonia, and related chemical species. An exemplary light transmitting sensing element is constructed comprising an aromatic heterocyclic polyimide doped with a pH indicating dye immobilized in the polymer matrix. The pH indicating dye may include xanthene dyes and triphenylmethane dyes, such as by way of example and not limitation: bromocresol purple (BCP), bromothymol blue (BTB), tropeolin, methyl orange, methyl red, and alizarine.

The invention may also be used to detect acidic gas analytes including $CO_2$ by reversing the polarity of the electrical output.

In one exemplary embodiment of the invention, a halogenated polyimide polymer is loaded with the indicator dye by dissolving the polymer and dye in a solvent compatible with both components and evaporating the solvent. The resulting sensing element is found to be insensitive to humidity and capable of operating for years without degradation. Further, polyimide is one of the highest temperature polymers available, indicating potential extended temperature operation.

The sensor may be further improved and increased in sensitivity by including nanoparticles that interact with the system to increase the coupling of the indicator dye to the optical sensing beam and to increase the chemical interaction of the sensed chemical and the indicator dye. A method of producing a polyimide polymer colloid with gold nanoparticles is disclosed wherein gold nanoparticles are produced in an organic solvent and the polymer and indicator dye are added to the solvent colloid.

Exemplary nanoparticles include gold, palladium, and platinum. Typical nanoparticle size may be 10 to 50 nanometers in diameter.

An exemplary test sensor was constructed using a halogenated polyimide, AMOCO ULTRADEL™ 0920D with bromocresol purple indicator dye. Gamma-butyrolactone (GBL) was used as a solvent in the preparation of the dye doped polymer. The resulting medium was found stable and insensitive to variations in humidity for sensing ammonia in air.

To further improve the sensitivity of the sensor, an embodiment is shown having a reference photodiode and differential amplifier to compensate for the fluctuations of the intensity of the light source. The light source may be pulse modulated and the output signal from the differential amplifier amplified with a lock-in amplifier synchronized by the same pulsed signal that drives the light source. One embodiment of the sensor is shown with a self calibration means comprising an electrically controlled valve and a reference container with a saturated vapor of the analyte.

The following disclosure describes an exemplary embodiment for measuring accurately the concentration of a basic gas pollutant, in particular ammonia, in ambient air, achieving improved sensitivity to the gas pollutant with good resistance to atmospheric moisture and ambient noise. Whereas, the details are directed to measuring ammonia in air, the teachings may also be applied to other analytes in other gas mixtures and generally to measuring trace chemicals in fluids.

FIG. 1 is a block diagram of an exemplary sensor in accordance with the present invention. Referring to FIG. 1, the sensor comprises a sensing module 101 that is placed in a chamber 102. The chamber 102 has inlet 103 for air, an air filter 104, a valve 105, a pump 106, and an outlet 107. A calibration container 108 with a saturated vapor of the gas to be measured is connected to valve 105. A computation and control module 109 is connected to the sensing module 101, valve 105, and pump 106.

Figure 2:
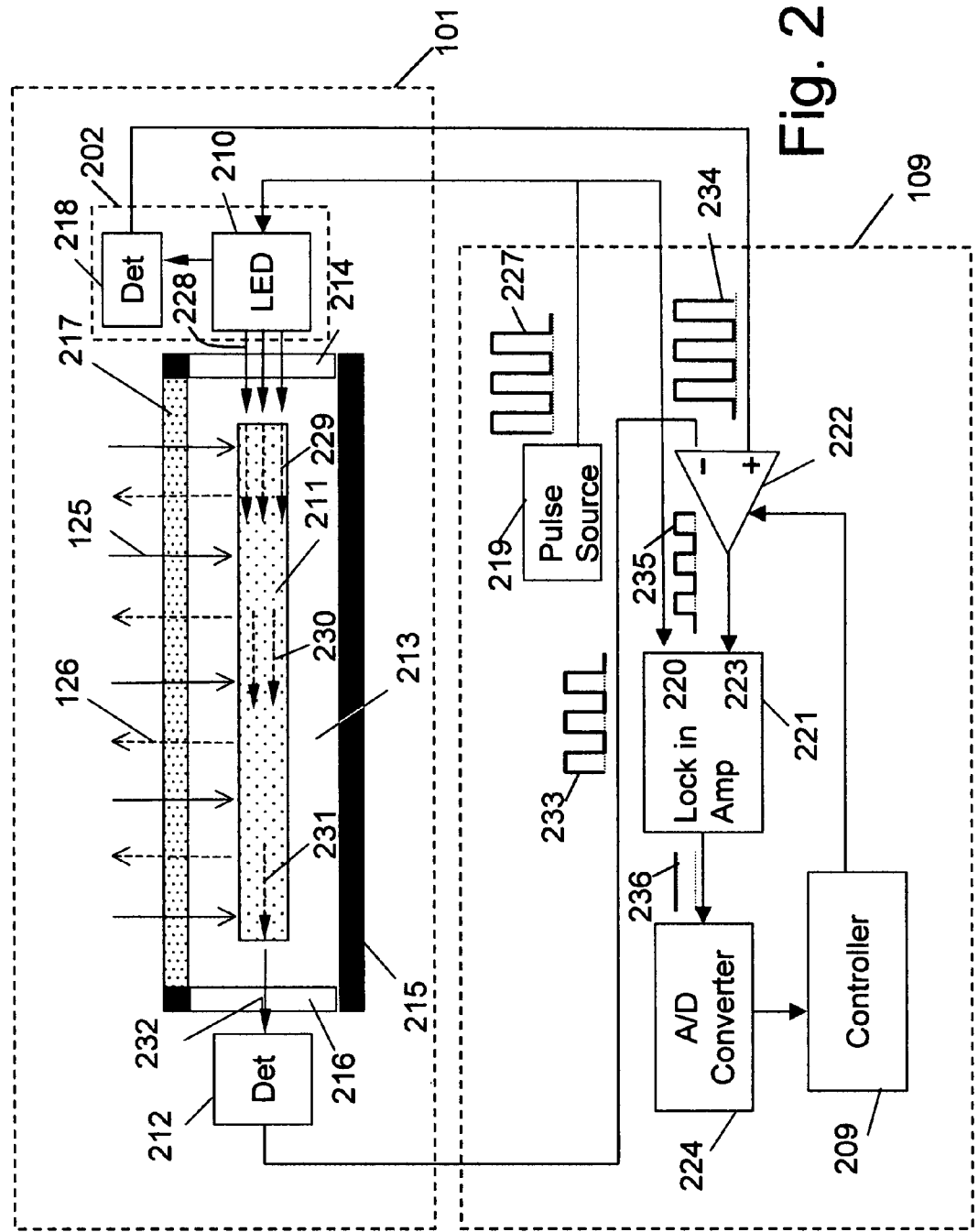
FIG. 2 is a block diagram of an exemplary sensing module for use in the sensor of FIG. 1.

FIG. 2 is a block diagram of an exemplary sensing module and controller for use in the sensor of FIG. 1. The sensing module 101 comprises three major components: a light source 210, a light transmissive element 211, and a photodetector 212. The light transmissive element 211 contains a porous polymer matrix with water included in the matrix. The matrix is doped with indicator dye sensitive to the pollutant and may have metal nanoparticles suspended in a desired concentration. Light transmissive element 211 is enclosed in cell 213. The cell 213 comprises input optical window 214, impermeable wall 215, output optical window 216, and gas permeable wall 217. The gas permeable wall allows the gas with analyte, air with ammonia to enter the cell and exit the cell containing the light transmisive element 211. An additional photodetector 218 is optically coupled to light source 210 for compensation of intensity variations of the light source. Electronic pulse generator 219 drives the light source 210 and the synchronization input 220 of a lock-in amplifier 221. A sensing photodetector 212 for sensing the attenuated light output of the light transmissive element 212 is connected to the inverting input of a differential amplifier 222, and the compensation photodetector 218 is connected to the noninverting input of the differential amplifier 222. The output of the differential amplifier 222 is connected to the signal input 223 of the lock-in amplifier 221 to detect the signal component of the differential amplifier output which is synchronous with the pulse generator 219. The output of the lock in amplifier 221 is converted to digital using an analog-to-digital converter 224, and the digital value is provided to computation and control module 209. The control module may also drive the gain and bias of the differential amplifier 222 to calibrate the system.

Figure 3:
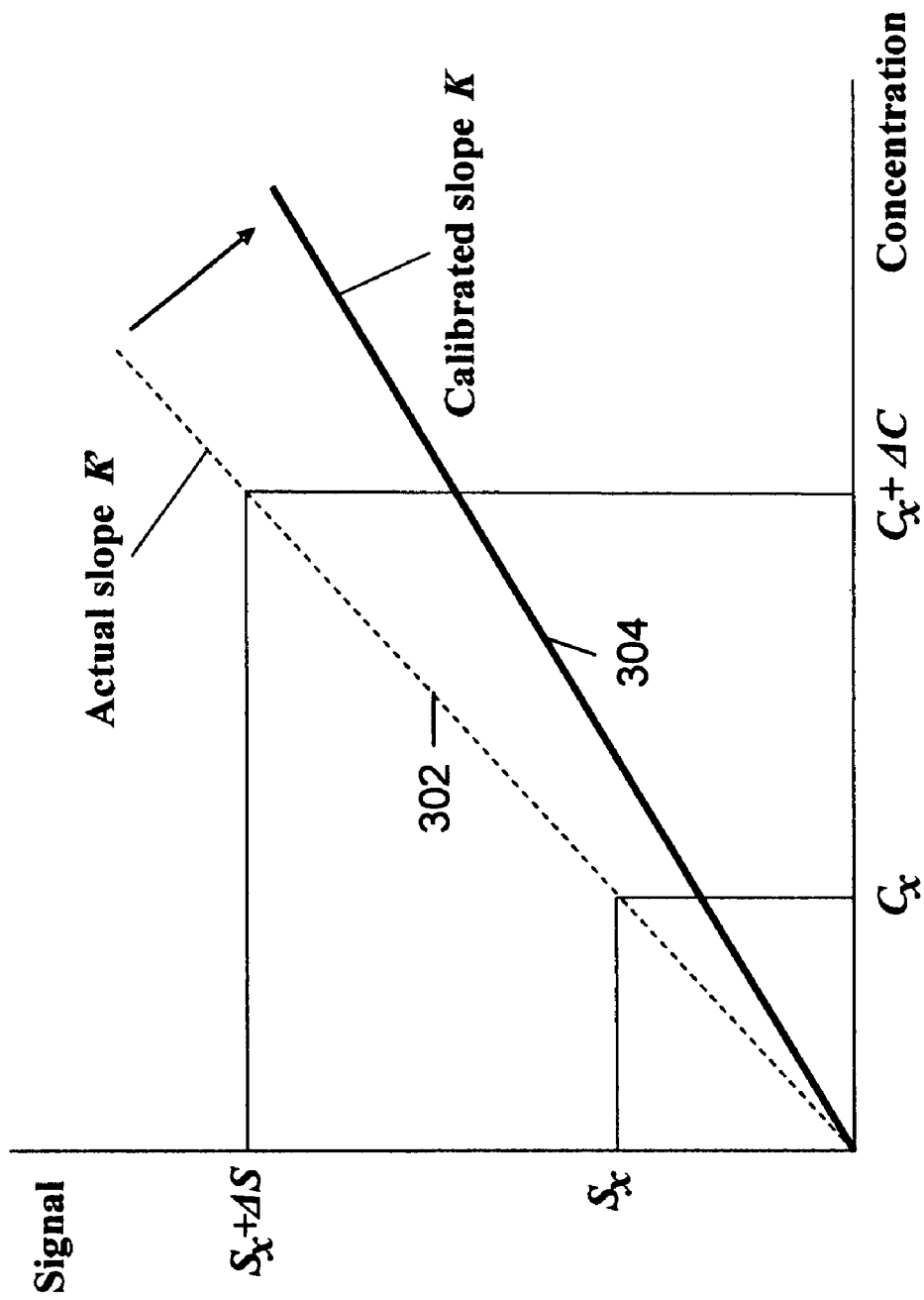
FIG. 3 shows two gain slopes as they are used in an exemplary self calibration procedure.

Functional operation of the sensor can be understood from FIGS. 1, 2, and 3. Air containing a pollutant or other chemical gas to be measured enters chamber 102 through inlet 103 and filter 104 (FIG. 1). The air enters sensing module 101 as shown by arrows 125 and exits it as shown by arrows 126. Miniature air pump 106 ejects air from chamber 102 through outlet 107. Pulse generator 219 generates a train of periodic pulses 27 that cause light source 210 to generate periodic flashes of light. Light beam 228 from the light source 210 enters light transmissive element 211 through window 214. Light beam 229 is attenuated in element 211 due to absorption and scattering as indicated by reducing number of rays in light beam 230 in the middle of the path through the element 211 and beam 231 at the end. Residual (attenuated) light beam 232 exits the light transmissive element 211 and enters photodetector 212 through window 216. Photodetector 212 converts the periodic flashes of light 232 to a train of electric pulses 233 that are sent to the inverting input of the differential amplifier 222.

Simultaneously, part of the light produced by source 210 is sent to compensation photodetector 218. The compensation photodetector 218 converts a portion of the light from the light source 210 to a train of pulses 234 that are sent to the non-inverting input of amplifier 222. The amplifier produces a periodical signal 235 that is equal to the difference between pulsed signals produced by the two photodetectors 218 and 212. Signal 235 goes to signal input 223 of lock-in amplifier 221. The lock-in amplifier produces DC signal 236 that is proportional to the amplitude of the pulses in signal 235. Signal 236 is sent to an analog-to-digital (A/D) converter 224. The A/D converter sends digital data to a computation and control module 209.

In one embodiment, the signals from the sensing photodetector 212 and the compensation photo detector 218 are adjusted in amplitude to be equal at the differential amplifier 222 inputs when the sensor is exposed to pure air—air having zero ammonia content (adjustment not shown).

Air with ammonia enters cell 213 from chamber 102 (FIG. 1) through the gas permeable wall 217 and diffuses through cell 213 to the light transmissive element 211 as indicated by arrows 125. The pollutant reacts with the indicator dye immobilized in the polymer matrix of light transmissive element 211 and changes the absorption of light by the indicator dye. The reaction is enhanced by nanoparticles embedded and immobilized in the light transmissive element 211. Some portion of the pollutant diffuses out 126 of element 211 back in chamber 102. Eventually, dynamic equilibrium is reached between the number of molecules of the gaseous pollutant entering and leaving element 211. The increased light attenuation due to the presence of the pollutant results in a drop of the amplitude of signal 233 that is subtracted from reference signal 234 in amplifier 222. Correspondingly, the amplitude of the pulses in signal 235 increases proportionally to the concentration of the pollutant in air. Thus, the DC voltage 236 increases proportionally to the concentration of the analyte.

DC voltage 236 is measured by A/D converter and used to determine the value of the concentration of the analyte by control module 209, which may display or output the value as needed.

One function of the gas permeable wall 217 is to protect the transmissive element 211 from contamination by dust, mists, condensation, and other factors. A range of wall types, or barriers may be used. The wall may be a filter, such as a HEPA filter commonly used for air conditioners or vacuum cleaners. Alternatively, a porous polytetrafluoroethylene (PTFE) sheet such as Mupor™ PM3T may be used. The PTFE sheet repels liquid water in addition to dusts. A further alternative may be a metal or plastic screen or even a blocking plate. The sensor may work without any gas permeable wall protection, but at the risk of contamination. Too much filter, however, slows the response of the sensor to the analyte.

A further function of the gas permeable wall 17 is to block ambient light. Ambient light entering the light transmissive element may flood the light sensor. Some amount of ambient light rejection is provided by using the pulsed light source and lock-in amplifier to detect the light. Nonetheless, too much ambient light may shift the detector bias point and change the detector gain or saturate the detector, contributing to errors.

In one embodiment, the sensor may include a self calibration mechanism. A problem with self calibration in the field is the availability of contamination free air for the calibration. The problem may be solved in accordance with the following procedure by measuring a known increment in sample gas and calibrating the gain of the system accordingly based on the increment rather than on an absolute known value. The self calibration mechanism includes a sample of the substance to be detected and a calibrated release mechanism.

FIG. 3 shows plots of two linear functions "Signal versus Concentration" as they are used in an exemplary self calibration procedure. The following self-calibration procedure may be used to calibrate the sensor in the field using available contaminated air as the input air source. Periodically, control module 209 opens valve 105. Container 108 has approximately the same number of molecules per unit of volume in saturated vapor of pollutant produced by solid powder material or liquid. When valve 105 opens up, the injection of pollutant from container 108 in air brings the concentration of pollutant up by two approximately constant increments $\Delta C_1$ and $\Delta C_2$ corresponding to two particular speeds of air pump 106 controlled by control module 209. These known increments are added to a certain, not exactly known concentration $C_x$ of pollutant in air (FIG. 3). After computational corrections of all nonlinearities the signal of the sensor is supposed to be a linear function of concentration with a calibrated linear slope K and zero bias B=0; graph 302 of the dependence "signal S versus concentration C" stored in control module 209. However, due to aging or fluctuations in electronic circuits the actual slope and bias can change from K to K' and B=0 to B'≠0, graph 304. Computation and control module 209 remembers the signal of the sensor $S_x$ before opening valve 205 and knows the new signals $S_{new\ 1}$ and $S_{new\ 2}$ after adding pollutant at two different rates. It computes the actual slope and bias as $K'=(K_1'+K_2')/2$ and $B'=(B_1'+B_2')$ where $K_1'=(S_{new\ 1}-S_x)/\Delta C_1$, $K_2'=(S_{new\ 2}-S_x)/\Delta C_2$, $B_1'=2 S_x+K_1'\Delta C_2-S_{new\ 2}$, and $B_2'=2 S_x+K_2'\Delta C_1-S_{new\ 1}$. Then control module 209 sends command to differential amplifier 222 to re-program the amplifier 222 gain and bias and to bring the overall slope and bias back to standard values K and B=0 respectively thus completing self-calibration of the instrument.

Referring to FIG. 1, the calibration sample container 108 is a container with a liquid or solid substance and is capable of producing and releasing a sample of the analyte in a controlled manner. For example, in the case of an ammonia sensor, a liquid sample can be ammonium hydroxide $NH_4OH$ (ammonia dissolved in water) or Refrigerant 717 (liquefied ammonia). A solid sample can be a pellet of hexaaminemagnesium chloride $Mg(NH)_3Cl_2$. The free volume of the container is filled up with the saturated vapor of the analyte and compressed pure air. At a given temperature T, there is always the same saturated molar concentration CS of the analyte in the air inside the container. The pressure of the gas mixture inside container $P_1$ is also determined by temperature T. For instance, at room temperature (20 degrees Celsius) the pressure of ammonia-air mixture over the surface of hexaaminemagnesium chloride $Mg(NH)_3Cl_2$ is approximately 1.05 normal atmospheric (normal atmospheric pressure is $1.033\times10^5$ Pa or 760 Torr). The saturated concentration of ammonia $C_s$ is 150 ppm. When valve 105 opens up, the mixture of analyte gas with pure air from the container enters chamber 102 and mixes with ambient air coming in. The molar rate at which the analyte gas flows in chamber 102 in moles per second can be computed using formula Molar rate of analyte [mole/s]=$C_s FeA[2(P_1-P_2)P_1/(MRT)]^{1/2}$, where F=0.6 is the coefficient of discharge; $e=1-0.41(1-P_2/P_1)/\chi$ is the isentropic coefficient of the analyte gas ($\chi$=1.4 for air); A is the cross-sectional area of the orifice of valve 105; $P_2$ is the atmospheric pressure; M is the molar mass of the analyte gas; R=8.31 J/(mole.K) is the universal gas constant; T is the temperature.

For instance, for the saturated vapor of ammonia in container with hexaaminemagnesium chloride $Mg(NH)_3Cl_2$ considered before and the cross-sectional area of the orifice A=0.04 mm$^2$, the Molar rate of analyte (ammonia, M=17 g) is equal to $3.6\times10^{-7}$ mole/s.

The rate at which ambient air enters chamber 102 is determined by the speed of pump 106. Usually, the speed of a pump is characterized by volumetric rate. The molar rate can be computed using equation Molar rate of air [mole/s]=Volumetric rate of pump [m$^3$/s]$\times P_2/(RT)$.

For instance, if pump 106 is set by controller 109 to operate at a Rate of pump of 100 cm$^3$/s ($10^{-4}$ m$^3$/s), the Molar rate of air will be $4.24\times10^{-3}$ mole/s.

The increment of the concentration $\Delta C$ of the analyte gas in ambient air entering chamber 102 can be calculated as $\Delta C$=Molar rate of analyte/($C_s^{-1}$ Molar rate of analyte+ Molar rate of air)

For the case presented above, the increment $\Delta C$ is 54.2 ppm. This well defined value can be used for self-calibration of the sensor.

Test Sensor

An exemplary test sensor was constructed to measure ammonia in air. Light transmisive element 211 was made of a halogenated polyimide AMOCO ULTRADEL™ 9020D doped with commercial indicator dye Bromocresol Purple (BCP)$C_{21}H_{16}Br_2O_5S$. No nanoparticles were included.

Further details on the structure of materials related to AMOCO ULTRADEL™ 9020D may be found in: Cahill, Pa., et al. "Polyimide Based Electrooptic Materials" Nonlinear Optical Properties of Organic Materials VI, 13 Jul. 1993, Society of Photo-Optical Instrumentation Engineers, pp 48-55, which is hereby incorporated herein by reference.

The following chemical reactions occur during the interaction of the light transmissive element 211 with ammonia:

$$NH_3+H_2O \leftrightarrow [NH_4]^+ + OH-, \quad (1)$$

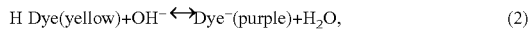

$$H\,Dye(yellow)+OH^- \leftrightarrow Dye^-(purple)+H_2O, \quad (2)$$

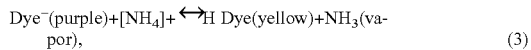

$$Dye^-(purple)+[NH_4]+ \leftrightarrow H\,Dye(yellow)+NH_3(vapor), \quad (3)$$

Reactions (1) and (2) take place when molecules of ammonia diffuse into the polymer. Deprotonization of the dye molecule causes its optical absorption to change. The color of the dye switches from yellow to purple. The reading of the change is provided by an optical means. Reaction (3) takes place when ammonia diffuses out of the polymer. The initial color is then restored.

Figure 4:
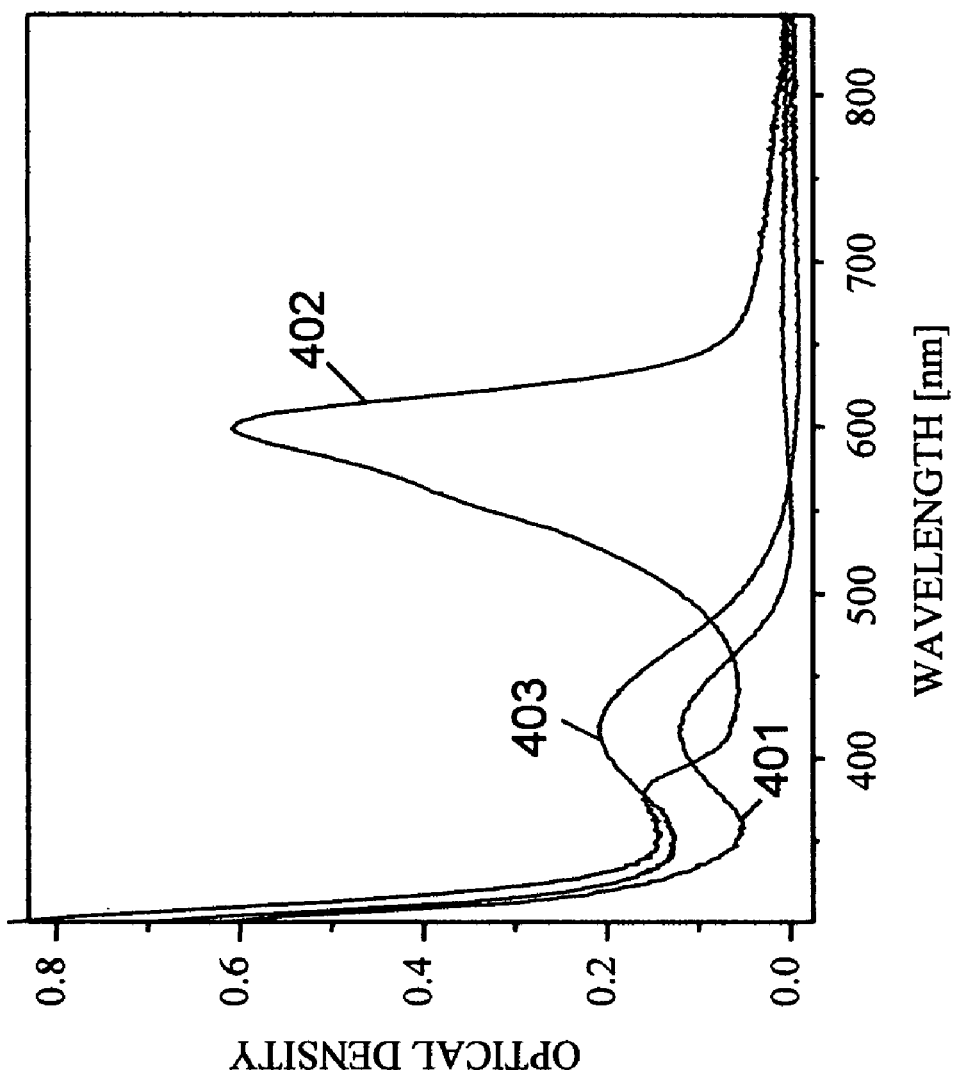
FIG. 4 illustrates the spectra of optical absorption of the doped polymer before and after exposure to ammonia.

FIG. 4 illustrates the spectra of optical absorption of the doped polymer before and after exposure to ammonia. Referring to FIG. 4, a freshly made sample of polymer film (with dye) has no absorption peaks in the visible region and is colorless and clear in appearance. Initial pre-exposure to a relatively high concentration of ammonia activates the film and, upon removal of the ammonia, the film has a permanent (non reversible) absorption peak at 410 nm (curve 401). The doped polymer becomes light yellowish. After that, any exposure to ammonia brings up a reversible absorption peak at 590 nm corresponding to purple color of the indicator dye (curve 402. Removal of the ammonia brings the 590 nm peak reversibly down and the color returns back to the yellowish color due to the 410 nm absorption peak. After several periodic exposures the 410-nm peak reaches a stable height (see curve 403 in FIG. 4), and the unexposed sample becomes deep yellowish.

Figure 5:
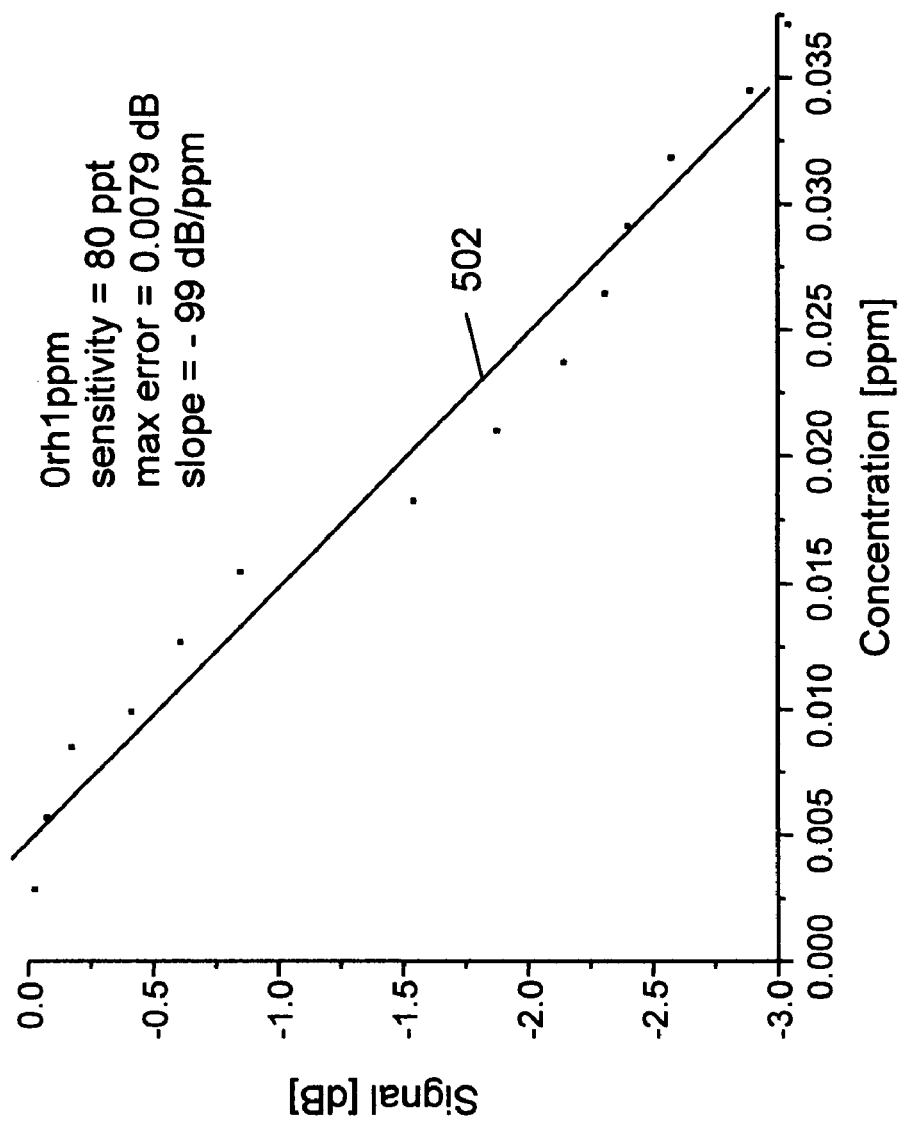
FIG. 5 shows a calibration plot of the sensor.

FIG. 5 shows a calibration "Signal (in dB) versus Concentration" plot of the test sensor. The plot is inversed with respect to similar plot depicted in FIG. 3. Correspondingly, the slope is negative instead of positive as in FIG. 3. The sensor was tested after running continuously in the laboratory for four years. The minimum detectable concentration (also called sensitivity) is estimated as 80 ppt (parts per trillion, $10^{-12}$) by comparing the slope of the curve 502 in FIG. 5 to the RMS measurement noise level.

Sensitivity of the sensor is defined as the minimum detectable concentration $C_{min}$ of the substance to be detected (analyte). In order to be detectable, this minimum concentration should produce the change of the signal of the sensor $\Delta S_{min}$ at least equal to the level of noise N. Based on these to definitions, the sensitivity was calculated as Senstivity [ppm]=$C_{min}$[ppm]=$\Delta S_{min}$[dB]/$K$[dB/ppm]
=$N$[dB]/$K$[dB/ppm], where, K is the slope of the calibration plot "Signal versus Concentration" of the sensor. The equation points to two major avenues of improvement of sensitivity: (a) increasing slope K by adding more indicator dye to the polymer host or adding more nanoparticles; (b) reducing noise.

Figure 6:
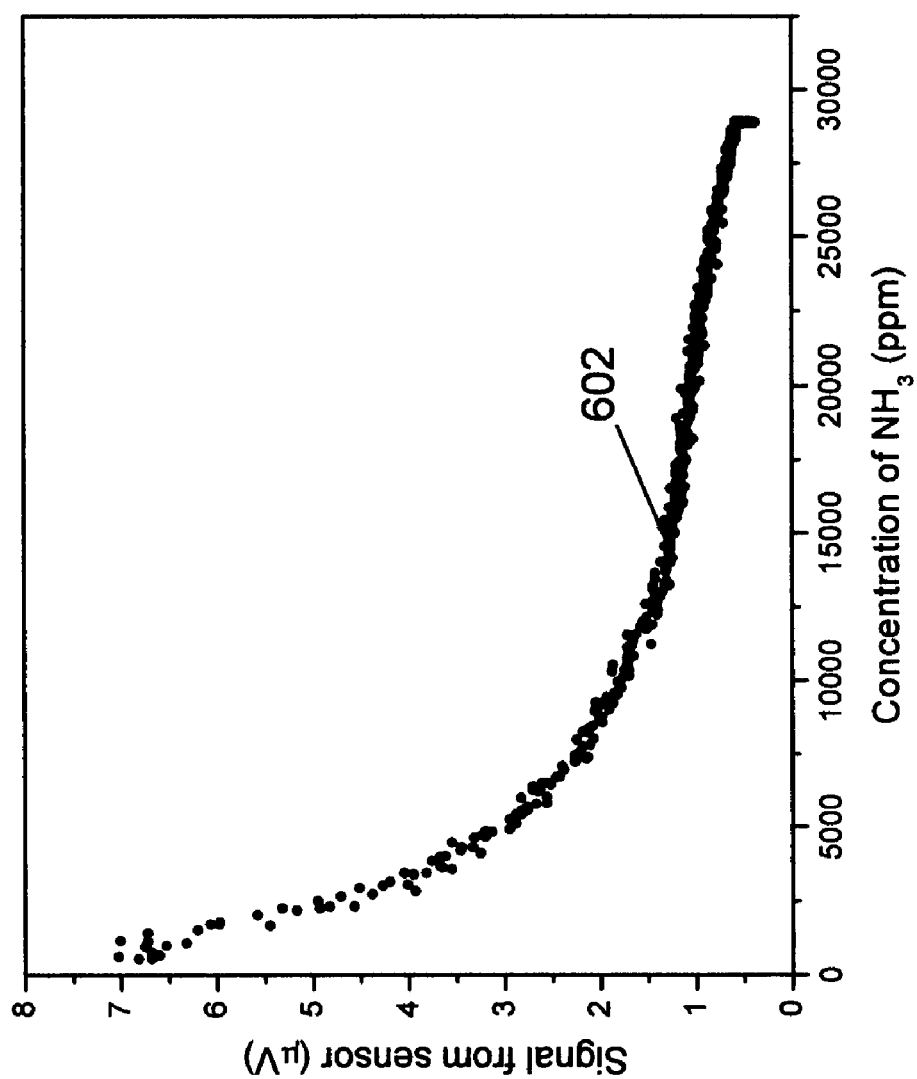
FIG. 6 shows the sensor response at high concentration levels.

FIG. 6 shows the sensor response at high concentration levels. The sensor potentially has a very wide dynamic range. At higher concentration, the sensor's sensitivity automatically drops down as can be seen from curve 602 of FIG. 6. The slope of the calibration plot "Signal vs. Concentration" decreases almost exponentially with the concentration. Thus, the same sensing module 101 can be used to measure concentrations within an extremely wide relatively linear range from 0 to 5000 ppm (parts per million) with extended sensing to 30,000 ppm (3%) (mole fraction). Exposure to even 3% ammonia does not damage the sensor.

Figure 7:
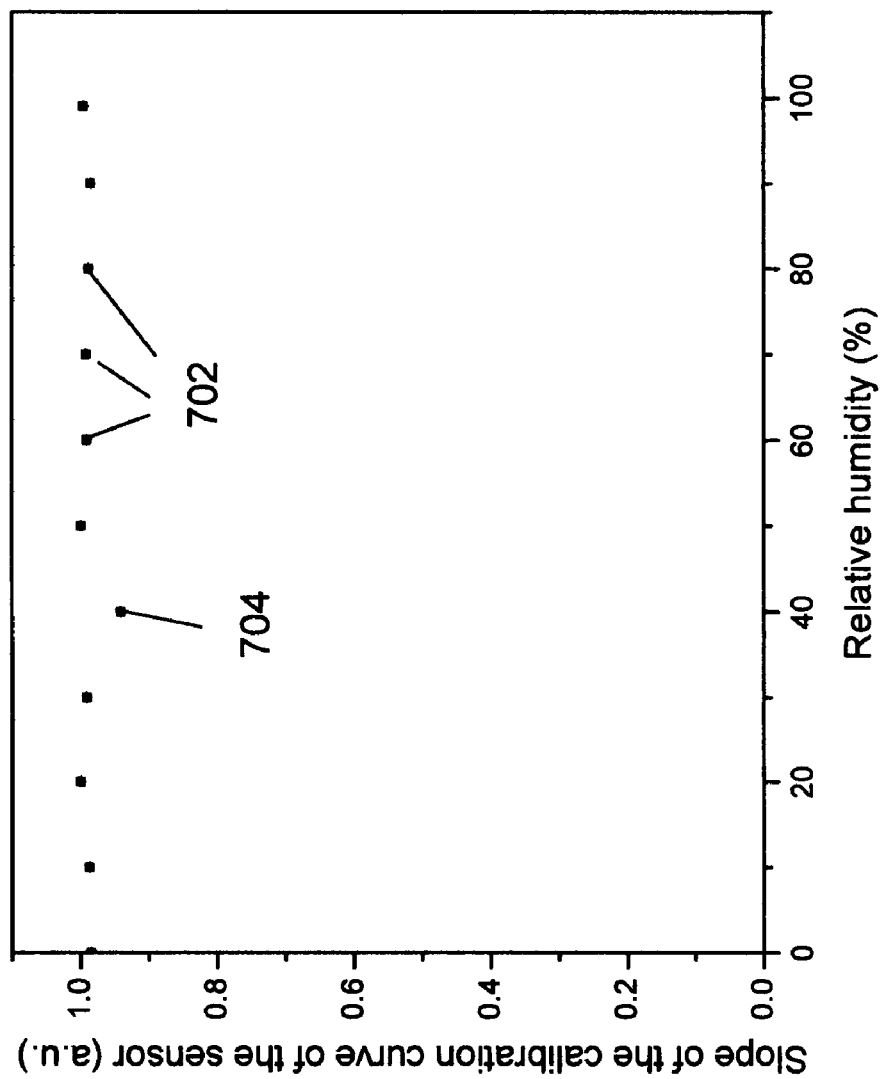
FIG. 7 shows the slope of the calibration plot as a function of humidity.

FIG. 7 shows the slope of the calibration plot "Signal versus Concentration" as a function of humidity. The slope of the calibration plot "Signal vs. Concentration" was determined for a number of different atmospheric humidity values (points 702). Note that the slope did not change significantly when the relative humidity of ambient air was changed from zero to 100% (FIG. 7). The one point 704 that deviates from the remaining points 702 is suspected to be due to a data error. Even assuming the point 704 is without error, the slope was consistent to within ±3% from a median value. Neglecting that point, the slope was consistent to within ±1%. Thus, the sensor has demonstrated that it is relatively insensitive to atmospheric humidity.

Polyimide has been shown to be hygroscopic to a significant degree. One reference (Reference 10) finds a particular polyimide to be capable of 3.2% by weight moisture uptake. Another reference (Reference 6) finds the thickness and dielectric constant variation with humidity can be used as a moisture sensor. U.S. Pat. No. 4,761,710 describes another moisture sensor based on polyimide. The inventors have found; however, that when used as a medium for a pH indicator dye, the moisture uptake does not appear to affect the operation of the pH indicator dye within the polymer. In contrast, the inventors expect the ability to uptake moisture is a benefit where the polymer is allowed to achieve equilibrium moisture content. The inventors expect that other polymers exhibiting similar hygroscopic properties (preferably capable of 1% or greater moisture uptake) may also exhibit stable characteristics when used as a medium for an indicator dye.

Test Sensor with Nanocolloid

In another configuration of the sensor, the light transmissive element of the ammonia sensor was made as before using the polyimide AMOCO ULTRADEL 9020D doped with bromocresol purple (BCP), but with nanoparticles of gold added to form a nanocolloid. The nanocolloid was prepared in a solvent capable of dissolving the polymer together with indicator dye.

AMOCO ULTRADEL 9020D resin is a highly fluorinated pre-imidized polyimide based on hexafluorisopropylidene dianhydride (6FDA) and trifluoro methyl (CF3) groups (BPDA/FAPB) with an alkylated photocross-linking group incorporated in its backbone. The resin is typically supplied dissolved in gamma-butyrolactone (GBL) solvent at a concentration of 7 to 15 weight percent solids. The fluorinated polyimide has lower optical attenuation compared with typical non-fluorinated polyimides. The ULTRADEL polyimide is also designed for photo polymerization, but this feature is not necessary and is not used in the making of this sensor.

Incorporating gold nanoparticles in the resin to produce the polyimide-gold nanocolloid presents further challenges. Metal colloids are typically supplied as aqueous colloids not easily mixed with polyimide resin and not having a common solvent that would not cause precipitation of the solids. The problem was solved by producing a gold colloid directly in a solvent compatible with the polyimide.

A solvent colloid suspension of nanoparticles may be produced by the following process using a pulsed laser to generate the nanoparticles: A micropowder of a material of interest (gold, palladium, and platinum have been demonstrated) may be prepared by grinding or mechanical crushing. The prepared micropowder is suspended in an organic solvent where the polymer host can be dissolved (for example, carbon tetrachloride, $CCl_4$). The solvent should be selected with care because many solvents break down in the intense laser beam leaving carbon or other products in the suspension. Chlorobenzene broke down in one test. Good transparency at the laser wavelength is one criteria for a potential solvent.

A beam produced by a pulsed laser is directed vertically downwards and focused by a focusing lens in the suspension below the surface. A Q-switched Nd:YAG laser with a 9 ns 0.1 Joule pulse was used at a 10 pulse per second rate. The peak intensity of the pulsed beam in the focus is of the order of 10 $GW/cm^2$ or higher. The focused beam generates a concentration of energy that, it is believed, may evaporate the metal and solvent in a micro-plasma at the focus of the beam. The condensing metal then forms nanoparticles in the cool liquid solvent. In addition, the beam may generate a spark-like plasma with forces that crush or pulverize microparticles into nanoparticles. The tightly focused beam also seems to attract more microparticles to the focus by a substantial gradient electric force. Additionally, the shock wave produced by the plasma in the liquid assists in circulation of the suspension and delivery of the microparticles to the location of the focus for further crushing. The shock wave also generates a splash of suspension droplets streaming upward into the beam coming from above. The droplets also seem to receive sufficient energy to generate secondary spark effects which may result in additional processing of material, speeding the processing of a batch of microparticles. The apparent effects of electric attraction and shock wave from the plasma may dramatically increase the speed of the process In order to clean the resulting nanocolloid of residual micron- and submicron-size particles (particles larger than nanoparticles), the liquid can be processed in a centrifuge for 10 min at 14,000 rpm and separated from the precipitate.

Further details of the process may be found in Provisional application 60/817,197, which has been incorporated herein by reference.

The polyimide-gold nanocolloid was prepared as above by generating a nanocolloid of a solvent compatible with the polyimide resin. The polyimide is typically supplied as a resin in a solvent such as gamma-butyrolactone (GBL). The $CCl_4$ solvent used to generate the solvent-gold nanocolloid is compatible with the polyimide-GBL system. Thus, the solvent colloid may be added to the polyimide—dye-solvent solution.

The nanocolloid was added to the prepared solution of polymer and indicator dye and mixed with the solution using a magnetic stirrer.

The final polymer film with nanoparticles was applied to the substrate using dipping or spin casting followed by evaporation the solvent in a baking oven at a temperature 60° to 80° Celsius for one to three hours leaving the polyimide with indicator dye and gold nanoparticles incorporated within the polyimide. The baking oven was open to atmospheric air at about 40% humidity, i.e., there was no inert or dry nitrogen atmosphere during drying.

The open air drying was also used in the making of the first test polyimide sensor which was tested for sensitivity to atmospheric humidity. The open air drying allows the polyimide to absorb humidity from the air as the solvent evaporates from the matrix and may contribute to the low sensitivity of the resulting sensor to atmospheric humidity.

Note also that the sensor was prepared by dissolving the pre-imidized polyimide in a solvent and evaporating the solvent. The resulting matrix may be more open to humidity and allowing diffusion of ammonia than a structure generated by cross linking the starting materials for the polyimide. Thus, the step of evaporating the solvent from the polyimide solution may also contribute to the insensitivity of the resulting sensor to humidity.

The concentration of nanoparticles in the prepared polymer matrix was measured by weight percentage. Initially, the weight of micropowder added to the solvent was measured. After the nanocolloid was prepared and centrifugated, the weight of nanoparticles remaining in suspension was determined by subtracting the weight of the residual solid precipitate from the weight of the initial micropowder. The nanocolloid was added to the polymer solution with the weight of polymer known. In case of polyimide Ultradel 9020D the polymer was supplied from the manufacturer at 7 to 15% by weight in the solution. In case of a test sensor constructed using poly(methyl methacrylate) (PMMA), the polymer solution was prepared using 1 g of solid polymer per 10 mL of solvent. This provided for a known weight proportion of nanoparticles in the resulting polymer film after the solvent dried. The weight proportion of nanoparticles in polymer was kept within the range 0.5 to 2.5%. Below this range, the nanoparticles had minimal effect on the sensitivity of the sensing polymer film. Above this range, optical losses in the polymer film were too great for accurate detection of the transmitted light.

The inventors attribute at least part of the sensitivity of the device to surface plasmon resonance (SPR) of the nanoparticles in the polyimide medium. SPR is a phenomenon related to metals which have a negative real component of dielectric constant. This negative real component of dielectric constant interacts with a positive real component from a medium surrounding the nanoparticle to yield a resonant peak in the absorption or scattering characteristic.

The resonance of the nanoparticles at optical wavelengths near an active wavelength of the indicator dye is apparently responsible for increased coupling of the light to the indicator dye, resulting in increased absorption of the light due to the indicator dye. Thus, materials having known SPR properties may make good candidates for nanoparticles.

Further, other materials including, but not limited to, other polyimides, other polymers, and non-polymer media such as sol-gels, glasses, or even liquid solutions may be used with a nanoparticle having SPR properties and an indicator dye.

Figure 8A:
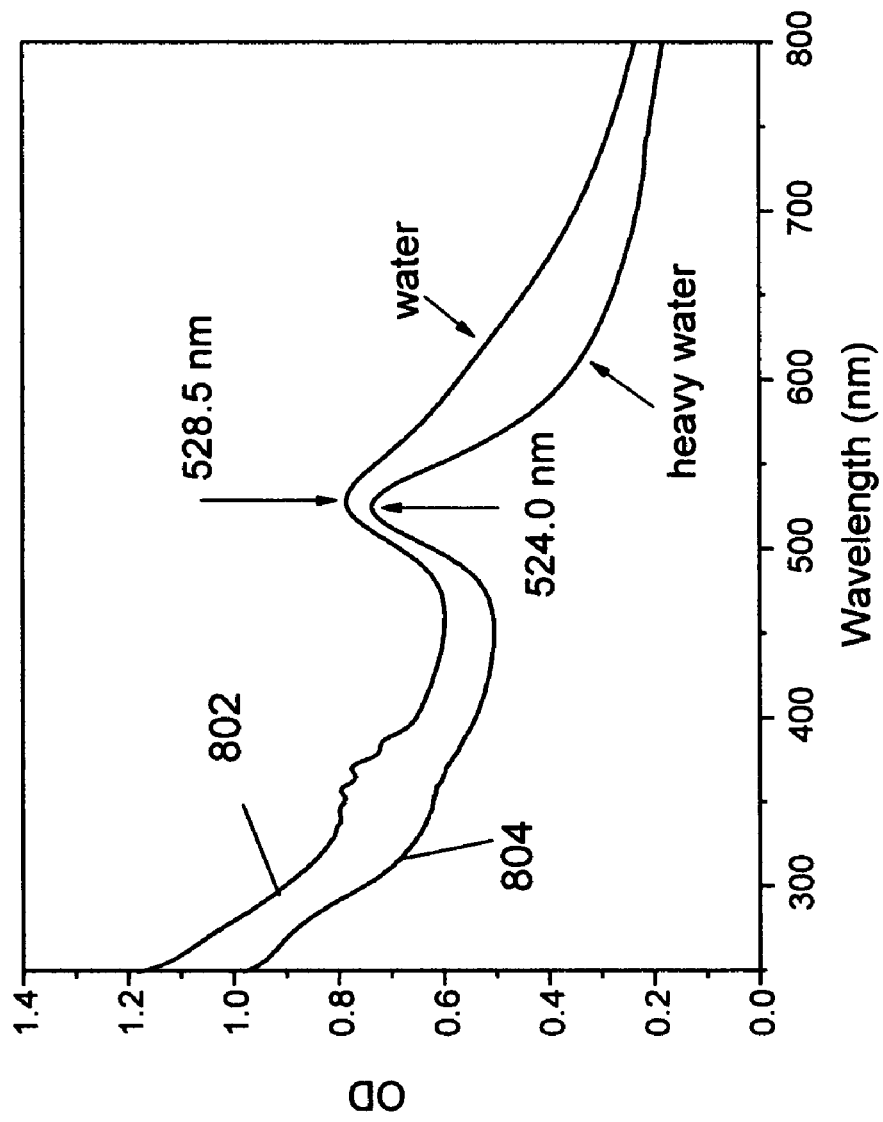
FIG. 8A shows the spectra of optical extinction for two samples of gold nanocolloid.

FIG. 8A shows the optical extinction spectra for two samples of gold nanocolloid in water. Curve 1 and curve 2 show a gold nanocolloid peak of optical attenuation associated with SPR in the wavelength region around 530 nm. The gold peaks can be seen to be near the peak of reversible absorption of the indicator dye (590 nm, see FIG. 4), suggesting that the resonance of the nanocolloid may couple to the waveband of the indicator dye. Since the SPR effect is dependent on the optical propagation properties of the medium, some shift in color may be expected for the same nanoparticles in polymer vs. the water suspension shown.

Figure 8B:
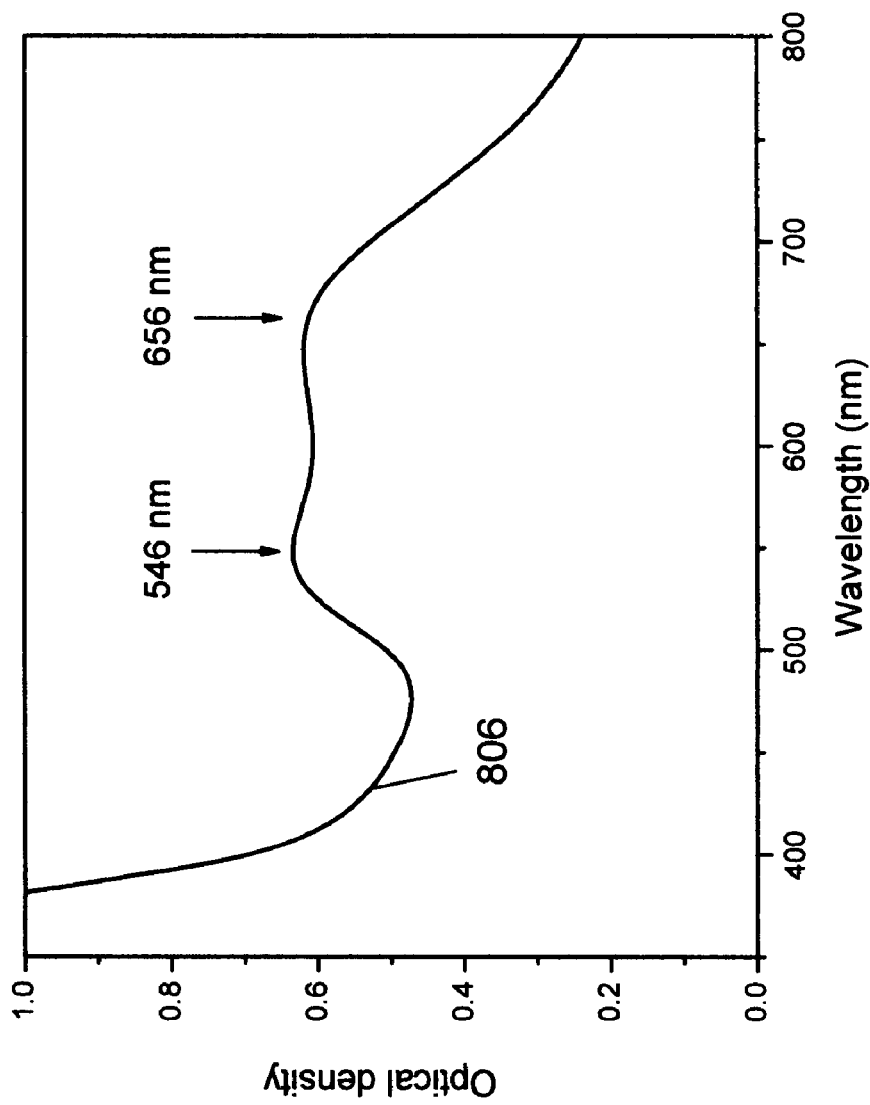
FIG. 8B shows the spectrum of optical extinction for a sample of gold nanocolloid in gamma-butyrolactone (GBL) solvent.

FIG. 8B shows the optical extinction spectrum for a sample of gold nanocolloid in GBL solvent. The nanocolloid was produced using the Nd:YAG laser spark process described herein. Note the two resonant peaks in curve 806 at 546 nm and 656 nm. This sample demonstrates that nanoparticles may be produced directly in the GBL solvent used with ULTRADEL 9020, eliminating the need for the additional carbon tetrachloride solvent. Thus, the sensor could be made by making a GBL-nanoparticle colloid and adding the GBL nanoparticle colloid to the polyimide—GBL solution, followed by evaporating the GBL solvent from the resulting mixture.

Nanoparticles may affect the sensitivity of the light transmissive element 211 through two mechanisms, the mechanism of the SPR and as catalysts for the reactions of Equations (1), (2), and (3) that determine the color of the indicator dye. Nanocolloids of gold, platinum, palladium, and other catalysts may potentially act through both SPR and catalyst action; whereas nanocoilloids of metals like copper and nickel may act only through the mechanism of SPR.

The difficulty of making a polymer with nanoparticles may be appreciated by considering potential alternative approaches. These approaches may be divided into (a) methods of making dry nanopowders first and then adding them to polymer solutions and (b) methods of preparing nanocolloids directly in polymer solutions.

Methods of making dry nanopowders are given in the US Government Report "Nanostructure Science and Technology: R&D Status and Trends in Nanoparticles, Nanostructured Materials, and Nanodevices." Kluwer Academic Publishers, 1999, Chapters 2, 7. These methods can be grouped into two major areas: (a) gas phase synthesis and (b) sol-gel or wet chemical processing. Nanoparticles with diameters ranging from 1 to 10 nm with consistent crystal structure, surface derivatization, and a high degree of monodispersity have been reportedly processed by both techniques.

Gas phase synthesis methods comprise (1) development of new crystalline materials based on nanoparticles generated by evaporation and condensation (nucleation and growth) in a sub-atmospheric inert-gas environment and (2) various aerosol processing techniques with high production yield of nanoparticles including synthesis by combustion flame; plasma; laser ablation; chemical vapor condensation; spray pyrolysis; electrospray; and plasma spray. A typical example is an atomization process LINA-Spark™ described in U.S. Pat. No. 5,369,035, Method and apparatus for analytical sample preparation, Eastgate et al., Nov. 29, 1994. In a related alternative, the heater may be an Nd-YAG laser and the material may be a solid. The beam of the pulsed Nd-YAG Laser is focused near the surface of the sample. The space above the sample is rinsed with fresh argon. Each laser pulse ionizes the argon and creates a plasma close to the surface of the sample. During its short life of one microsecond the plasma evaporates some material from the surface. The material condenses immediately in the argon, creating an extremely fine aerosol.

Sol-gel processing is a wet chemical synthesis approach that can be used to generate nanoparticles by gelation, precipitation, and hydrothermal treatment. Size distribution of semiconductor, metal nanoparticles can be manipulated by either dopant introduction or heat treatment. Better size and stability control of quantum-confined semiconductor nanoparticles can be achieved through the use of inverted micelles, polymer matrix architecture based on block copolymers or polymer blends, porous glasses, and ex-situ particle-capping techniques. Once nano-particles are produced, they can be separated from the liquid by drying out solvent, precipitation, or centrifugation.

The problem with the first alternative approach (making nanopowder first and adding to polymer later) is that the particles in the dry nanopowders have to be prevented from clumping back into larger-size chunks. Typically, the nanoparticles have to be coated (capped) with special surfactants, shells, etc. that may make the nanoparticles incompatible with the polymer matrix.

The sol-gel approach is a wet chemical method where the nanoparticles are prepared in the polymer solution. Typical example is the method of preparing a polymer nanocomposite described in U.S. Pat. No. 7,172,811, Denisyuk, et al. Feb. 6, 2007, "Methods of preparing polymer nanocomposite having surface modified nanoparticles". The method comprises: "(a) providing a first solution having a first organic solvent comprising a non-alkali metal salt, a carboxylic acid comprising at least one aryl group, and a polymer dissolved therein; (b) providing a sulfide material; (c) combining the first solution and the sulfide material; and (d) isolating the nanocomposite, wherein the nanocomposite comprises the polymer and a plurality of nanoparticles, wherein each nanoparticle comprises at least one metal sulfide nanocrystal having a surface modified with the carboxylic acid comprising at least one aryl group." Again, this method, as any other wet chemical processes, has limitations in terms of types of nanoparticles that can be incorporated into a particular polymer. Nanoparticles of many desirable materials cannot easily be made in this way.

Therefore, the inventors chose to find a way to make nanoparticles and introduce them into the polymer using compatible materials.

Alternative Configurations

Figure 9:
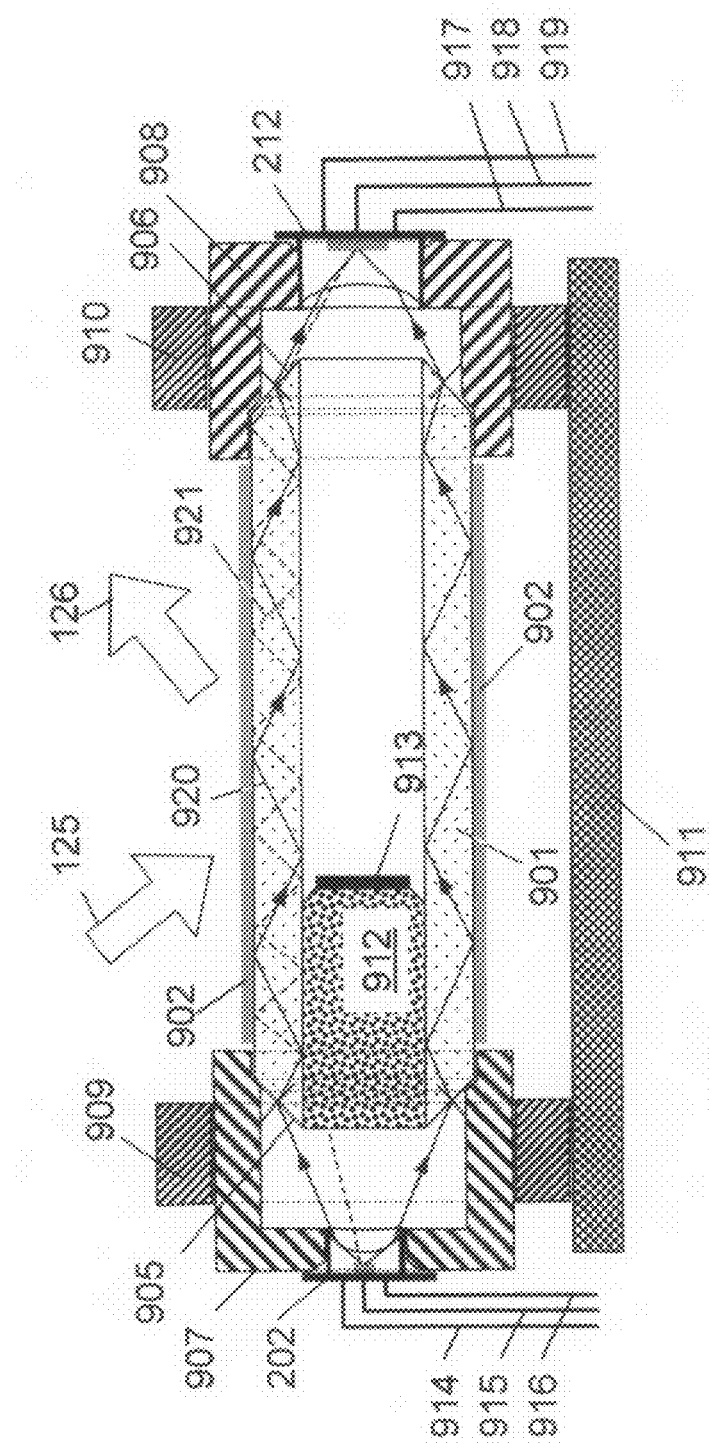
FIG. 9 illustrates an exemplary embodiment of the invention wherein the sensing material is coated on a transparent optical substrate.

FIG. 9 illustrates an exemplary embodiment of the invention wherein the sensing material is coated on a transparent optical substrate. Referring to FIG. 9, the sensor comprises glass capillary tube 901 coated with a dye-doped polymer film 902. Light source assembly 202 (light emitting diode assembly including the LED 10, with the reference photodiode 218 integrated into the same package) is optically coupled to one end of the capillary tube 901. The other end of the capillary tube 901 is optically coupled to light receiver 212 (photodiode). End 905 of the tube is beveled at an angle to maximize the number of internal reflections of the light rays propagating through the capillary tube 901. End 906 of the capillary tube 901 is shaped (beveled) to concentrate the rays from the capillary tube 901 onto the light receiver 212. Light source 202 is attached to the capillary tube 901 through a spacer 907. Receiver 212 is attached to the capillary tube 901 through spacer 908. Spacers maintain optimum distance between source 202 and receiver 212 from the ends 905 and 906 respectively. Holders 909 and 910 attach spacers 905 and 906 to base 911. The inner space of the tube 901 next to source 202 is plugged with a scatterer 912. The end of the scatterer inside the tube is covered by opaque light stopper 913. Light source assembly 202 has three leads: anode of the light emitting diode 914, common cathode 915, and anode of the monitoring photodiode 916. Receiver 904 has tree leads: anode 917, cathode 918, and ground 919.

In operation, ray 920 from source 202 enters tube 901 through face 905 and propagates bouncing between the inner and outer walls of the tube. When the ray approaches the outer wall, it interacts with sensitive layer 902; then the ray exits capillary tube 901 through face 906 and propagates towards receiver 212. Para-axial ray 921 enters scatterer 912 and experiences scattering towards the tube where it bounces between the walls interacting with sensitive layer 902. Eventually ray 921 exits the tube through face 906 and propagates towards receiver 212. Stopper 913 blocks all the rays that might penetrate through the scatterer without being scattered off axis of the tube 901. When a gas, such as ammonia, diffuses in the sensitive layer 902 along path 125, the optical absorption of the layer increases and, correspondingly, the intensity of the light passing through tube 901 into receiver 212 decreases. When the gas diffuses out of layer 902 along path 126, the optical absorption of the sensitive layer 902 reversibly decreases and the intensity of the light arriving at receiver 212 increases. Input face 905 is shaped in a way to increase the number of reflections of the rays for source 202 from the outer wall of tube 901 coated with layer 902. Output face 906 is shaped in a way to concentrate the exiting rays in receiver 212.

In one exemplary embodiment, a test sensor was made wherein the outer diameter of tube 901 was 6.35 mm and the inner diameter was 4.19 mm. The tube had a length of approximately 39.4 mm. Ends of the tube were shaped to make a bevel of approximately 45°. Coating 902 was made by dipping the tube in a solution of polymer poly(methyl methacrylate) (PMMA) (from Eastman Kodak Corporation) in chlorobenzene (1 gram solids per 10 ml liquid) with indicator dye Bromocresol Purple (BCP) from Sigma-Aldrich added at a proportion 35 mM/L (milli moles/liter). The solution was made using a magentic stirrer at a temperature of 83° C. and then filtered with a 0.2-μm PTFE filter from Fisher Scientific. After dipping in the solution, the tube was shaken to remove the excess of the solution from the tube's surface and obtain a relatively uniform coat. The tube was then dried in a baking oven for 1 hour at a temperature of 100° C. The light source assembly 202 was L610/PD010-35D52 from Epitex with an LED 210 having a peak of emission spectrum at 610 nm and a monitoring photodiode 218 mounted with the LED. The receiver 212 was silicon photodiode ODD-5W-ISOL from Opto Diode Corporation. The light source 202 was powered by a pulsed flasher at 5-kHz pulse repetition rate. Insert 912 was made of a PTFE (TEFLON®) cylinder with slightly beveled ends and with a diameter of slightly less than 4.19 mm and with a length of 6.35 mm. There was no light stopper 913 used because most of the light was scattered out to the sides of the insert before reaching the inner end of the insert. A light scattering stopper, such as insert 912, may be used to stop light from passing straight through the tube and coupling to the output without passing through the sensing element. A light scattering stopper may be used in preference to an absorptive light stopper because the scattering light into the sensing path increases the efficiency of coupling of light from the LED to the sensing path. A translucent light spreader such as insert 912 allows lateral scattering of a portion of the light into the tube at angles that will propagate to the receiver 212.

Figure 10:
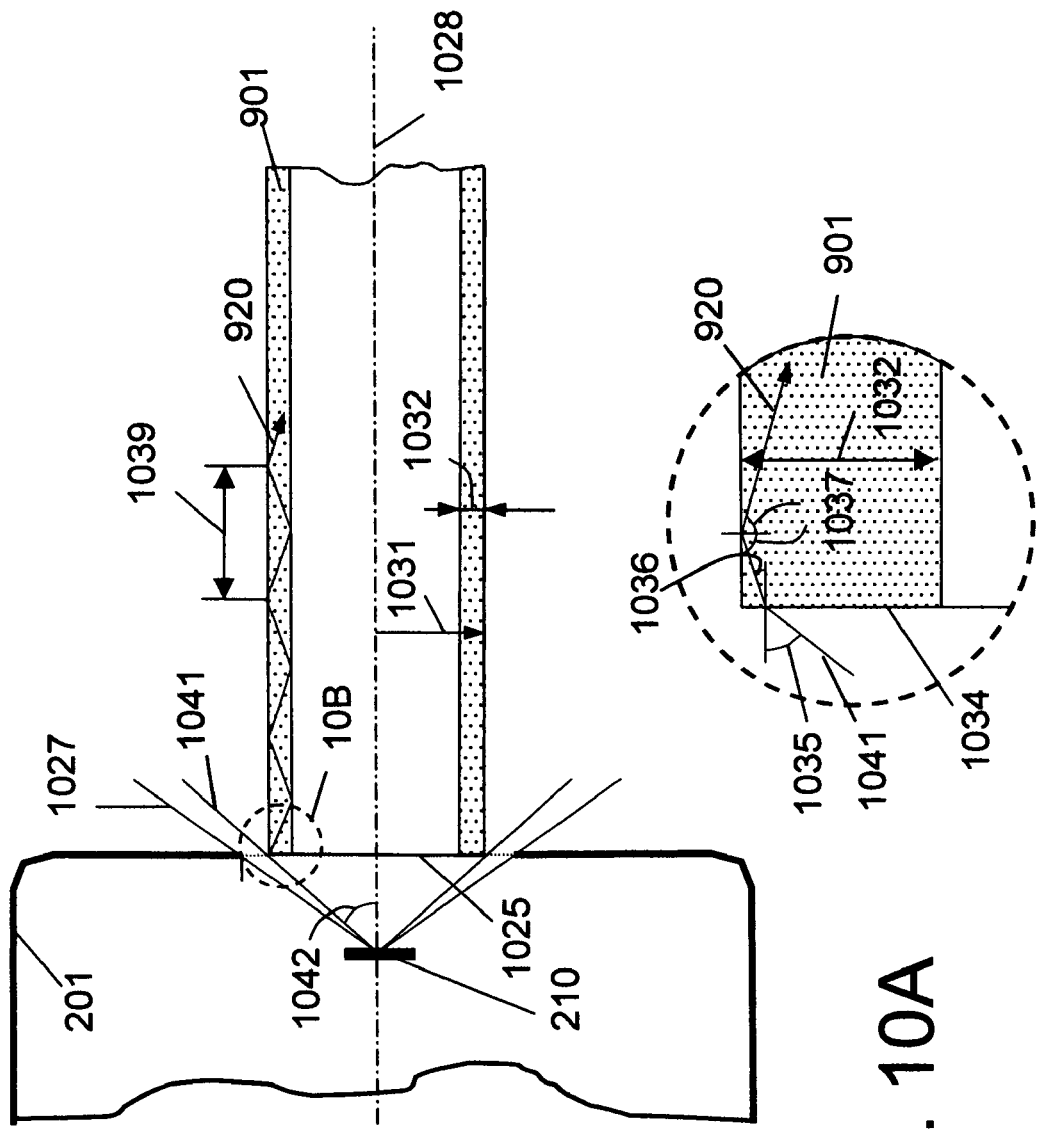
FIGS. 10A and 10B illustrate an exemplary embodiment wherein the tube is smaller in diameter than the width of the window of the illuminating LED.

FIGS. 10A and 10B illustrate an exemplary embodiment wherein the tube 901 is smaller in diameter than the width of the window 1025 of the illuminating LED 202. FIG. 10B is a magnified portion of FIG. 10A. Referring to FIGS. 10A and 10B, light source 210 is enclosed in body 201 with semi-flat glass lens window 1025. Light source 210 together with lens 1025 makes a cone of light rays with the outermost rays 1027 coming close to the edge of window 1025. Some of the rays miss tube 901. The outermost ray 1041 that strikes the tube propagates at angle 1042 with respect to axis 1028. Angle 1042 is half-view angle $\theta_{1/2}$. The tube 901 is in mechanical contact with window 1025 of the LED package. The outermost ray 1041 enters side wall 1034 at angle of incidence 1035 $i=\theta_{1/2}$ and is refracted at angle of refraction 1036 r that obeys the Snell's law $$\sin r = n_t^{-1} \sin i = n_t^{-1} \sin \theta_{1/2}, \quad (4)$$

where $n_t$ is the index of refraction of tube 901. Refracted ray bounces 920 between the outer and inner walls of the tube 901 at angle 1037 θ due to the total internal reflection. Angle 1037 θ is equal $$\theta = 90° - r. \quad (5)$$

If angle 1037 is less than the critical angle of total internal reflection of tube 901 $\theta_c$ as $$\theta > \theta_c, \quad (6)$$

where $$\theta_c = \sin^{-1}(n_t^{-1}), \quad (7)$$

then ray is internally reflected at the same angle 1037. Resulting ray 920 will be bouncing between the outer and inner walls of the tube being contained in the side wall. If the outer wall is coated with an absorbing sensitive layer, each reflection from the outer wall will bring losses to ray 920. Distance between the adjacent points of reflection of ray 920 from the outer wall 1039 α can be determined as $$\alpha = 2t \tan \theta \quad (8)$$

where t is the thickness of the side wall of tube 901. The shorter distance 1039, the more reflections ray 920 experiences from the outer wall per unit of length of tube 901 and the better is the sensitivity of the sensor to the increase of the optical absorption of the sensitive coating due to presence of the analyte gas. In one possible configuration of this embodiment, source 210 may be LED L610/PD010-35D52 (610-nm wavelength). Tube 901 may be made of borosilicate glass, having a critical angle, $\theta_c$, for total internal reflection of 41.5° ($\theta_c = \sin^{-1}(n_t^{-1}) = 41.5°$). The radius 1031 of the tube 901, R=1 mm; the thickness 1032 of side wall, t=0.25 mm; the half-view angle 1042 $\theta_{1/2}$=50°, angle 1037 is θ=59.5°>41.5°. The distance 1039 between reflections of the ray 920, α=0.84 mm. The number of reflection per 10-mm length is 12.

In a further aspect of the invention, the optical coupling may include an index matching cross-linking gel, such as NyGel® or other clear silicone adhesive, between the window of LED 210 and face 905 of tube 901 in order to (1) reduce reflection losses of the rays entering the tube 901; (2) provide a vibration absorbing soft layer between the optical parts preventing them from scratching and/or otherwise damaging one another.

Figure 11:
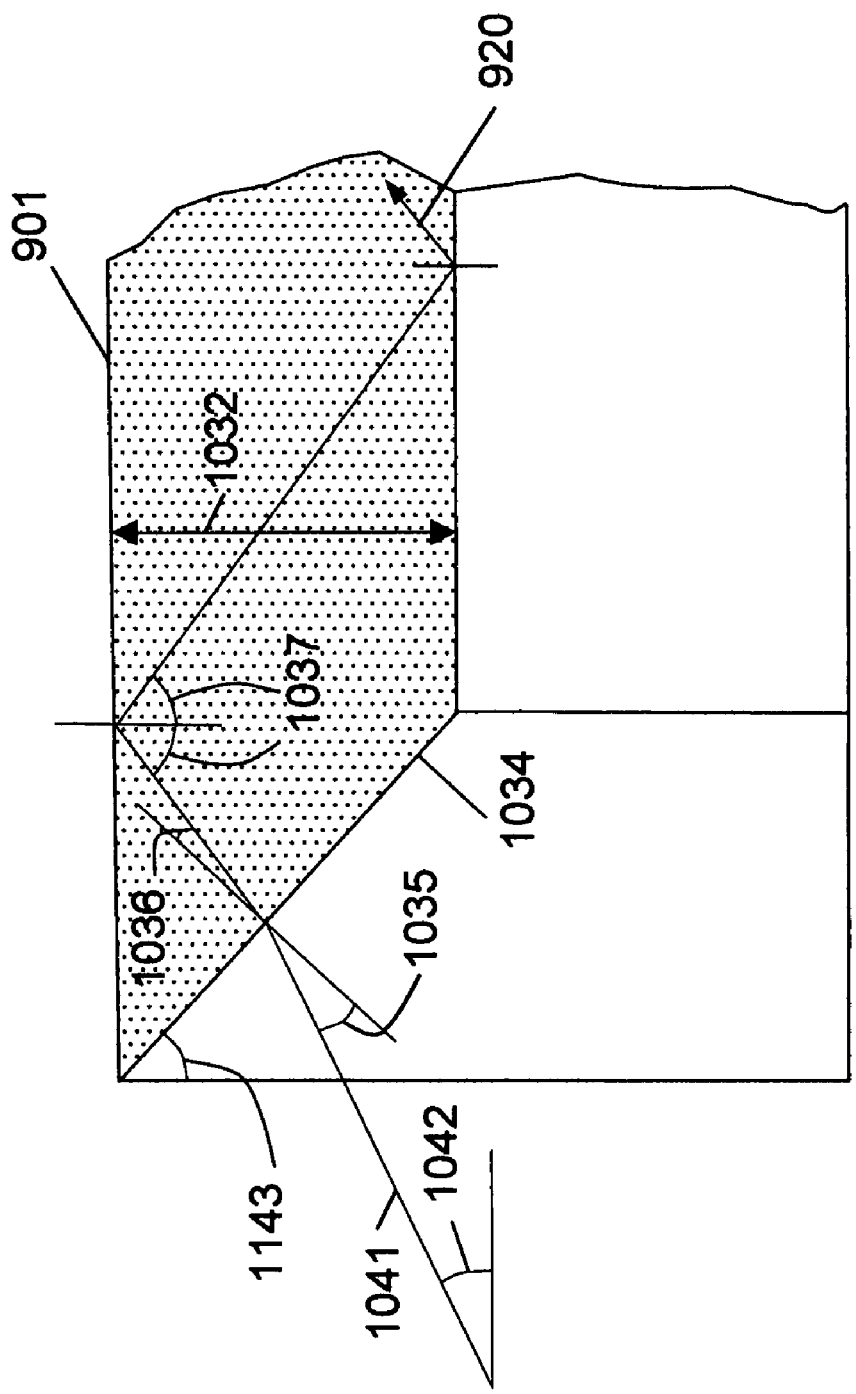
FIG. 11 illustrates a beveled tube end for improved coupling of the LED light to near critical angle propagation through the tube.

FIG. 11 illustrates a beveled tube end for improved coupling of the LED light to near critical angle propagation through the tube. Referring to FIG. 11, one way to reduce distance 1039 between reflection points is to make incident angle 1037 (FIG. 10), θ, as close to the critical angle $\theta_c$ as practical. This can be done by beveling face 1034 of tube 901 inward, as shown in FIG. 11. Angle 1143, α, of the beveled face 1034 must satisfy the inequality:

$$\alpha < (90° - \theta_c) + \sin^{-1}[n_i^{-1} \sin(\theta_{1/2} - \alpha)]. \quad (9)$$

In case of the tube diameter smaller than the LED window 1025 (as illustrated in FIG. 10A), half-view angle $\theta_{1/2}$ must be substituted by angle 1042 of the outermost ray from light source 210 entering the tube. The solution of Equation (9) can be found by numerical methods only. However, in one particular configuration, angle 1143 can be assumed α=45°. That means that ray 1041 from LED 210 enters face 1034 slightly refracted in the tube 901. For the practical example $\theta_{1/2}$=55°. The inequality in Eq. (9) is satisfied, since α=45°<90°−$\theta_c$+6.6°=90°−41.5°+6.6°=55.1°. In fact, beveling face 1034 at 45° is relatively easy from the manufacturing viewpoint. Angle of 1037 in this case will be determined as $$\theta = 90° + r - \alpha, \quad (10)$$

or θ=90°+6.6°−45°=51.6°. Distance 1039 between the points of reflection determined by Eq. (8) will be α=0.63 mm for the borosilicate tube 901 with 0.25-mm side wall described as an example of the previous embodiment. The number of reflections will be 16 per 10 mm of length, an improvement comparing to the previous 12. Beveling face 1034 thus helps to increase the number of reflections and to increase the sensitivity of the sensor.

CONCLUSION

Thus, herein described is a chemical sensor and method of making that allows for the sensing of a chemical analyte in a fluid such as a gas or liquid. Particular embodiments have been shown capable of measuring ammonia in air with high sensitivity and a high tolerance to variations in atmospheric humidity.

Attributes of the present invention that address the need for a field deployable sensor include:

1) a high sensitivity is achieved with a simple and reliable device, resistant to contamination and tolerant of a wide temperature range;

2) the device is relatively unaffected by atmospheric relative humidity;

3) the effects of noise originating from the fluctuations of the intensity of the light source as well as the noise produced by ambient light and the photodetector is attenuated; and 4) a self-calibration feature for periodic self calibration in the filed may be provided.

The present invention has been described above with the aid of functional building blocks illustrating the performance of specified functions and relationships thereof. The boundaries of these functional building blocks have been arbitrarily defined herein for the convenience of the description. Alternate boundaries can be defined so long as the specified functions and relationships thereof are appropriately performed. Any such alternate boundaries are thus within the scope and spirit of the claimed invention. One skilled in the art will recognize that these functional building blocks can be implemented by discrete components, application specific integrated circuits, processors executing appropriate software and the like or any combination thereof.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the appended claims and their equivalents.

REFERENCES (1) Dakin, J., and Culshaw, B., Optical fiber sensors. Vol. 4: Applications, Analysis, and Future Trends, Artech House, Boston, 1997 pp 53-80 and pp 95-97.

(2) Boisde, G., and Harmer, A., Chemical and biochemical sensing with optical fibers and waveguides, Artech House, Boston, 1996 pp 65-84.

(3) Klein, R., and Voges, E. I., "Integrated optics ammonia sensor," Advances in fluorescence sensing technology, edited by J. R. Lakowicz and R. B. Thompson, Proceedings of SPIE, Vol. 1885, SPIE, Bellingham, Wash., 1993, 81-92.

(4) Caglar, P., and Narayanaswamy, R., "Ammonia-sensitive fibre optic probe utilizing an immobilized spectrophotometric indicator," Analyst, Vol. 112, 1987, pp. 1285-1288.

(5) Hartman, N. F., Walsh, J. L., Campbell, D. P., and Akki, U., "Integrated optic gaseous NH3 sensor for agricultural applications," Optics in Agriculture, Forestry, and Biological Processing, edited by G. E. Meyer and J. A. DeShazer, Proceedings of SPIE, Vol. 2345, SPIE, Bellingham, Wash., 1995, pp. 314-323.

(6) Bowman, E. M. and Burgess L. W., "Evaluation of polymeric thin film waveguides as chemical sensors," Chemical, Biochemical, and Environmental Fiber Sensors II, Proceedings of SPIE, Vol. 1368, SPIE, Bellingham, Wash., 1990, 239-250.

(7) Lieberman, R. A., Ferrell, D. J., Schmidlin, E. M., Syracuse, S. J., Khalil, A. N., Mendoza, E. A., "Reversible sensor for carbon monoxide based on dye-doped porous fiber optic fiber," Proceedings of SPIE, Vol. 1796, SPIE, Bellingham, Wash., 1992, 324-331.

(8) Zh. Qi, A. Yimit, K. Itoh, M. Murabayashi, N. Matsuda, A. Takatsu, and K. Kato, Composite optical waveguide composed of a tapered film of bromothymol blue evaporated onto a potassium ion-exchanged waveguide and its application as a guided wave absorption-based ammonia gas sensor, Opt. Lett., Vol. 26, No. 9, 2001, 629-631.

(9) J. F. Giuliani, H. Wohltjen, Reversible optical waveguide vapor sensor, U.S. Pat. No. 4,513,087, Jan. 31, 1983.

(10) Pranjoto, Hartono and Denton, Denice "Gravimetric measurements of steady state moisture uptake in spin coated polyimide films" Journal of Applied Polymer Science Vol 42, Issue 1, abstract for pp 75-83, 10 Mar. 2003

What is claimed is:

1. A chemical sensor comprising:
    an optical transmissive element comprising:
        an indicator dye having an optical attenuation characteristic responsive to the presence of said chemical;
        a medium permeable by said chemical for supporting said indicator dye within said medium; and
        nanoparticles within said medium for enhancing the response of said indicator dye to said chemical;
    an optical source coupled to said optical transmissive element, said optical source providing light at a wavelength associated with said optical attenuation characteristic of said indicator dye; and
    a first optical detector coupled to said optical transmissive element to receive said light transmitted through said optical transmissive element, said first optical detector producing a first signal responsive to said light transmitted through said optical transmissive element;
    wherein said medium comprises a polyimide polymer;
    wherein said indicator dye is a triphenylmethane pH indicator dye.

2. The chemical sensor of claim 1, wherein said optical source is driven by a modulated waveform and said signal from said optical sensor is detected synchronously with said modulated waveform.

3. The chemical sensor of claim 2, further including a second optical detector configured to detect a portion of light from said optical source, wherein said second optical detector provides a second signal which is compared with said first signal from said first optical detector to compensate for variations in the intensity of said optical source.

4. The chemical sensor of claim 1, wherein said nanoparticles consist substantially of gold, platinum, or palladium.

5. The chemical sensor of claim 1, wherein the polyimide is a halogenated polyimide.

6. The chemical sensor of claim 1, further including a transparent optical substrate, wherein said optical transmissive element comprises a layer deposited on said transparent optical substrate and said optical source and said first optical detector are coupled through said optical substrate to said optical transmissive element.

7. The chemical sensor of claim 6, wherein said substrate is arranged to pass said light through said optical transmissive element multiple times before being detected by said first optical detector.

8. The chemical sensor of claim 1, further including a calibration sample of said chemical and a controller, wherein said controller releases a controlled concentration of said calibration sample to said optical transmissive element and adjusts a calibration of said sensor based on a response of said sensor to said controlled concentration of said calibration sample.

9. The chemical sensor of claim 1, wherein the light source is a non-coherent source.

10. The chemical sensor of claim 9, wherein the non-coherent source is a light emitting diode.

11. A chemical sensor for sensing a chemical in a variable humidity atmosphere comprising:

an optical transmissive element comprising:
  an indicator dye having an optical attenuation characteristic responsive to the presence of said chemical; wherein said indicator dye comprises a triphenylmethane dye;
  a hygroscopic polymer permeable by said chemical for supporting said indicator dye within said hygroscopic polymer; said hygroscopic polymer comprising polyimide; and
  nanoparticles within said medium for enhancing the response of said indicator dye to said chemical;
an optical source coupled to said optical transmissive element, said optical source providing light at a wavelength associated with said optical attenuation characteristic of said indicator dye; and
an optical detector coupled to said optical transmissive element to receive said light transmitted through said optical transmissive element, said optical detector producing a signal responsive to said light transmitted through said optical transmissive element.

12. The chemical sensor of claim 11, wherein said polyimide comprises a hexafluorisopropylidene dianhydride group or a trifluoromethane group.

13. A method for preparing a sensing element for sensing a chemical, comprising the steps of:
  preparing a metal-solvent colloid comprising an organic solvent having metal nanoparticles suspended therein;
  combining said metal-solvent colloid with a solution containing a hygroscopic polymer and an indicator dye to yield a composite mixture, said indicator dye having an optical attenuation responsive to said chemical, said metal nanopartices adapted to enhance the response to said chemical of said optical attenuation;
  evaporating said solvent from said composite mixture to yield a polymer nanocolloid sensing element;
  wherein the polymer is a polyimide, and the indicator dye is a pH indicator dye; and
  wherein the pH indicator dye is a triphenylmethane dye.

14. The method of claim 13, wherein said solution containing said polymer contains gamma-butyrolactone.

15. The method of claim 13, wherein the weight percentage of said metal nanoparticles to said polymer is between 0.5% and 2.5%.

16. The method of claim 13, wherein said polymer nanocolloid sensing element exhibits an optical resonance peak at a wavelength where said pH indicator dye is responsive to said chemical.

17. The method of claim 13, wherein said metal nanoparticles comprise a material that is a catalyst for a reaction of said indicator dye responsive to said chemical.

18. The method of claim 13, wherein said metal nanoparticles can exhibit surface plasmon resonance in conjunction with said polymer.

* * * * *